(12) United States Patent
Puentener

(10) Patent No.: US 9,802,886 B2
(45) Date of Patent: Oct. 31, 2017

(54) PROCESS FOR MAKING LYSINE-GLUTAMIC ACID DIPEPTIDE DERIVATIVES

(71) Applicant: Hoffmann-La Roche Inc., Little Falls, NJ (US)

(72) Inventor: Kurt Puentener, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/348,093

(22) Filed: Nov. 10, 2016

(65) Prior Publication Data

US 2017/0057912 A1    Mar. 2, 2017

Related U.S. Application Data

(60) Division of application No. 14/539,126, filed on Nov. 12, 2014, now Pat. No. 9,522,874, which is a continuation of application No. PCT/EP2013/059759, filed on May 13, 2013.

(30) Foreign Application Priority Data

May 15, 2012   (EP) .................... 12168119

(51) Int. Cl.
  *C07C 261/00*  (2006.01)
  *C07C 269/06*  (2006.01)
  *C07C 271/22*  (2006.01)
(52) U.S. Cl.
  CPC .......... *C07C 269/06* (2013.01); *C07C 271/22* (2013.01); *C07C 2603/18* (2017.05)
(58) Field of Classification Search
  CPC .......................... C07C 269/06; C07C 2103/18
  See application file for complete search history.

(56) References Cited

PUBLICATIONS

Agnihotri et al.(Structure-Activity Relationships in Nucleotide Oligomerization Domain 1 (Nod1) Agonistic γ-Glutamyldiaminopimelic Acid Derivatives, J. Med. Chem. 2011, 54, 1490-1510 with an exact publication date on the Web of Wed., Feb. 7, 2011).*

* cited by examiner

*Primary Examiner* — Yevegeny Valenrod
*Assistant Examiner* — Blaine G Doletski
(74) *Attorney, Agent, or Firm* — Robert C. Hall

(57) ABSTRACT

The invention relates to compounds of the formula

I and to a process for making same and to the use of the products in the solid phase peptide synthesis. The compounds of formula I are versatile peptide intermediates for the solid phase peptide synthesis (SPPS) of peptide drugs which comprise a Glu-fatty alkyl side chain building block attached to a Lys-part of the peptide chain.

16 Claims, No Drawings

PROCESS FOR MAKING LYSINE-GLUTAMIC ACID DIPEPTIDE DERIVATIVES

CROSS REFERENCE TO RELATED APPLICATIONS

This application is a divisional of U.S. application Ser. No. 14/539,126 filed on Nov. 12, 2014, which is a continuation of PCT/EP2013/059759 filed on May 13, 2013, which claims priority to EP Patent Application No. 12168119.1 filed on May 15, 2012, the disclosures of which are all incorporated herein by reference in their entirety

SUMMARY OF THE INVENTION

The invention relates to compounds of the formula

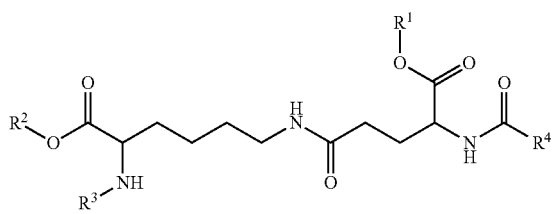

wherein,
$R^1$ and $R^2$ are the same or different and denote hydrogen or an ester protecting group,
$R^3$ is hydrogen or an amino protecting group and
$R^4$ is $C_{12-20}$-alkyl,
and its enantiomers, diastereomers and salts.

The invention in a further embodiment relates to a process for the preparation of the compounds of the formula I and to the use of the compounds of formula I in the solid phase peptide synthesis.

The compounds of the present invention have been found to be versatile peptide intermediates for the solid phase peptide synthesis (SPPS) of peptide drugs which comprise a Glu-fatty alkyl side chain building block attached to a Lys-part of the peptide chain. For example Liraglutide can be mentioned, which is a GLP-1 analog diabetes-2 peptide drug. Liraglutide carries a Glu-hexadecanoyl side chain building block at the Lys[26] position (Wikipedia, the free encyclopedia of 30 Apr. 2012)

Object of the present invention is to provide novel peptide intermediates which carry a Glu-fatty alkyl side chain and which can readily be inserted in the SPPS.

It was found that the compounds of the present invention of the formula

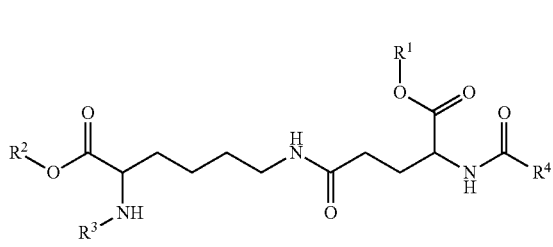

wherein,
$R^1$ and $R^2$ are the same or different and denote hydrogen or an ester protecting group,
$R^3$ is hydrogen or an amino protecting group and
$R^4$ is $C_{12-20}$-alkyl,
and its enantiomers, diastereomers and salts have the potential to very well serve this purpose.

DETAILED DESCRIPTION OF THE INVENTION

The term "$C_{12-20}$ alkyl" used for substituent $R^4$ refers to a branched or straight-chain monovalent saturated aliphatic hydrocarbon radical of twelve to twenty carbon atoms, particularly to a straight-chain monovalent saturated aliphatic hydrocarbon radical. The term can be exemplified by the radicals dodecyl, tridecyl, tetradecyl, pentadecyl, hexadecyl, heptadecyl, octadecyl, nonadecyl and eicosanyl.

In a particular embodiment $R^4$ refers to $C_{14-16}$ alkyl, even more particularly to $C_{15}$ alkyl.

More particularly $R^4$ is tetradecyl, pentadecyl or hexadecyl, but particularly pentadecyl.

The term "amino protecting group" used for substituent $R^3$ refers to common substituents conventionally used to hinder the reactivity of the amino group. Suitable amino protecting groups are described in "Fmoc Solid Phase Peptide Synthesis—A Practical Approach" W. C. Chan & P. D. White, Oxford University Press, 2000, reprinted 2004, printed digitally.

Particularly $R^3$ is Fmoc (9H-fluoren-9-ylmethoxycarbonyl).

The term "ester protecting group" used for substituents $R^1$ and $R^2$ refers to any substituents conventionally used to hinder the reactivity of the hydroxy group. Suitable hydroxy protecting groups are described in Green T., "Protective Groups in Organic Synthesis", Chapter 1, John Wiley and Sons, Inc., 1991, 10-142 and can be selected from $C_{1-4}$-alkyl, optionally substituted with phenyl, $C_{2-4}$-alkenyl, piperidinyl or dimethylaminoboranyl. Particular ester protecting groups for $R^1$ and $R^2$ are $C_{1-4}$-alkyl or $C_{2-4}$-alkenyl.

More particularly $R^1$ is t-butyl and $R^2$ is allyl.

The term "salts" in connection with the compounds of the present invention embrace the customary salts the skilled in the art would apply, such as hydrochlorides, acetates, trifluoroacetates or formiates.

In a particular embodiment of the invention $R^1$ is hydrogen or $C_{1-4}$-alkyl and $R^2$ is hydrogen or $C_{2-4}$-alkenyl.

In another more particular embodiment of the invention $R^1$ is t-butyl and $R^2$ is hydrogen or allyl.

In a particular embodiment of the invention the compounds of formula I have the formula

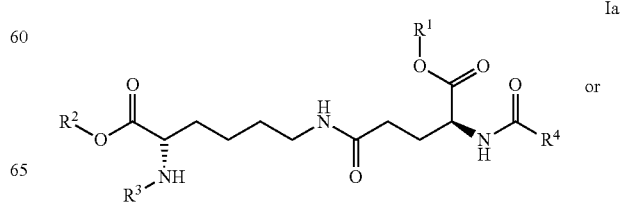

or

-continued

Ib

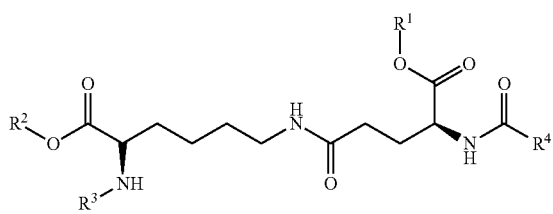

wherein,
R$^1$, R$^2$, R$^3$ and R$^4$ are as above and its enantiomers, diastereomers and salts.

The compounds of formula Ia or Ib with the substitution pattern as of below are even more particular embodiments of the invention:
R$^1$ t-butyl, R$^2$ hydrogen, R$^3$ Fmoc, R$^4$ C$_{15}$-alkyl, particularly pentadecyl.
R$^1$ t-butyl, R$^2$ allyl, R$^3$ Fmoc, R$^4$ C$_{15}$-alkyl, particularly pentadecyl.

In a more particular embodiment the compounds of formula I have the formula Ia. The compounds of the present invention can be prepared with processes which in principle are known to the skilled in the art of peptide synthesis.

For the preparation of compounds of formula I, wherein R$^2$ is hydrogen, the process comprises
a) coupling the glutamic acid derivative of formula

II

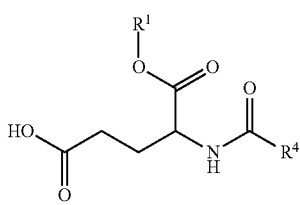

wherein R$^1$ and R$^4$ are as above, or a salt thereof with a lysine derivative of formula

III

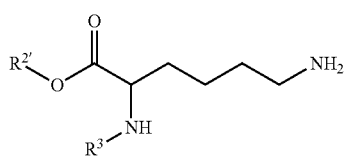

wherein R$^{2'}$ is an ester protecting group and R$^3$ is as above, or a salt thereof to form a compound of the formula Ic

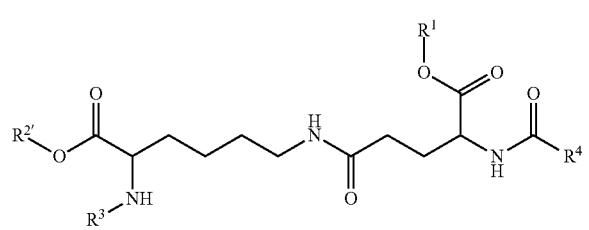

where
in R$^1$, R$^{2'}$, R$^3$ and R$^4$ are as above and
b) removing the ester protecting group R$^{2'}$.

Step a)

Step a) requires the coupling of the glutamic acid derivative of formula II with the lysine derivative of formula III.

The glutamic acid derivative of formula II can be prepared following the scheme 1 below starting from commercially available starting materials.

Scheme 1:

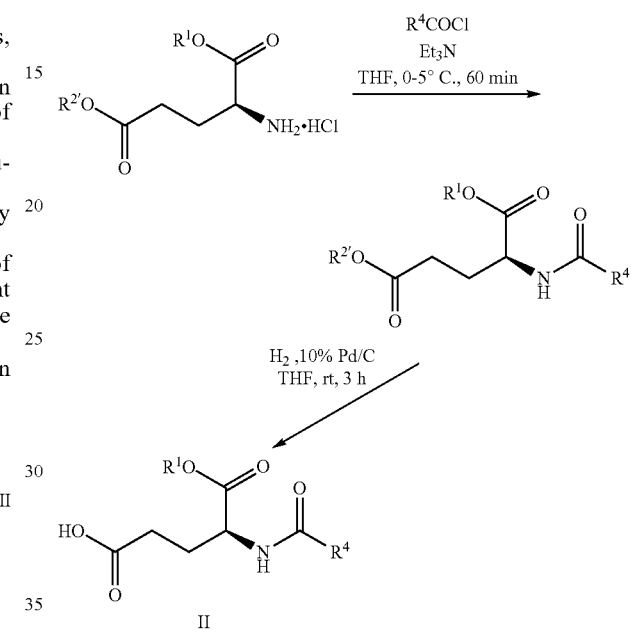

A suitable commercially available glutamic acid derivative of formula II is the (S)-5-benzyl 1-tert-butyl 2-aminopentanedioate hydrochloride.

The lysine derivatives of formula III are commercially available. Suitably the (S)-allyl 6-amino-2-(((9H-fluoren-9-yl)methoxy)carbonylamino)-6-aminohexanoate is used.

The coupling of the glutamic acid derivative of formula II with the lysine derivative of formula III can then be performed applying the classical techniques for peptide synthesis.

Accordingly the glutamic acid derivative of formula II is initially activated with an activating agent which is customary in the art such as with carbonyldiimidazole (CDI), carbodiimides selected from e.g. dicyclohexylcarbodiimide (DCC) or diisopropylcarbodiimide (DIC) or triazols selected e.g. from 1-hydroxy-benzotriazole (HOBt) or 1-hydroxy-7-aza-benzotriazole (HOAt).

Good results have been achieved with CDI (1,1'-carbonyldiimidazole) applied in a suitable organic solvent, like e.g. dichloromethane.

The coupling then can place with the lysine derivative of formula III in the presence of an organic base such as triethylamine, as a rule at room temperature.

The resulting dipeptide compound of formula Ib can be obtained from the organic phase by evaporation of the solvent and subsequent crystallization of the residue in a suitable organic solvent, such as in diethyl ether.

The compounds of formula Ib as subgenus of formula Ia outlined above, are particular embodiments of the present invention.

Particular representatives of compounds of formula Ib are (S)-allyl 2-(((9H-fluoren-9-yl)methoxy)carbonylamino)-6-((S)-5-tert-butoxy-5-oxo-4-palmitamidopentanamido) hexanoate with $R^1$=t-butyl, $R^{2'}$=allyl, $R^3$=Fmoc and $R^4$=pentadecyl.

Step b)

Step b) requires the removal of the ester protecting group $R^{2'}$ to form the compound of formula Ia.

This reaction is well known to the skilled in the art.

A suitable system for removing the allyl group is for instance a solution of a Pd-source, like tetrakis(triphenylphosphine)palladium(0) and of phenylsilane in an organic solvent such as dichloromethane, tetrahydrofuran or methyl tetrahydrofuran.

The reaction can take place at room temperature.

The resulting dipeptide of formula Ia can be obtained from the organic phase by evaporation of the solvent and subsequent digestion of the crude product with a suitable organic solvent such as with heptane and/or a mixture of heptane/dichloromethane.

As outlined above, the compounds of formula I can be used as versatile intermediates in the solid phase peptide synthesis, particularly in the synthesis of peptides which comprise a Glu-fatty alkyl side chain building block attached to a Lys-part of the peptide chain.

Even more particularly the compounds of formula I can be used in the FMOC solid phase peptide synthesis of such peptides.

EXAMPLES

Abbreviations:

r.t.=room temperature, DCM=dichloromethane, THF=tetrahydrofuran, TBME=tert.-butyl methyl ether, EtOAc=ethyl acetate, TLC=thin layer chromatography

Example 1

(S)-2-(((9H-fluoren-9-yl)methoxy)carbonylamino)-6-((S)-5-tert-butoxy-5-oxo-4-palmitamidopentanamido)hexanoic acid a) (S)-5-benzyl 1-tert-butyl 2-palmitamidopentanedioate

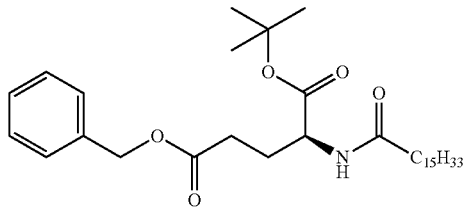

In a 200-mL, 3-necked flask, a mixture of (S)-5-benzyl 1-tert-butyl 2-amino-pentanedioate hydrochloride (5.00 g, 14.9 mmol), triethylamine (3.12 g, 30.7 mmol) and tetrahydrofuran (100 mL) was stirred at 0-5° C. for 15 min. To the suspension, palmitoyl chloride (4.35 g, 15.5 mmol) was added via a syringe within 10 min. The reaction mixture was stirred for additional 30 min at 0-5° C. As to TLC (EE/heptane 1:1, $R_F$ starting material=0.1, $R_F$ product=0.6, detected with aid of Komarowsky's reagent at 254 nm (cf. P. Stevens, *J. Chromatog.* 1964, 14, 269)) the conversion was complete. To the reaction mixture, water (60 mL) and tert-butyl methyl ether (70 mL) was added and the mixture was stirred at r.t. for 5 min. The organic layer was separated, washed with brine (120 mL), dried over sodium sulphate and evaporate to dryness to afford (S)-5-benzyl 1-tert-butyl 2-palmitamidopentanedioate (8.21 g, >99%) as a white solid with 98.9% chemical purity (LC method see below).

M.p. 47° C.; EI-MS: m/z=531.39 (M+H)⁺.

LC method: X-Bridge phenyl column No. 823, 50×4.6 mm, ID 2.5 μm; mobile phase, A: water/NCMe (95:5), B: NCMe, C: water/glycine (pH 9); flow: 3 ml/min; gradient from 50/4/55 (A/B/C) to 7/88/5 (A/B/C) within 2 min, isocratic 7/88/5 (A/B/C) for 0.8 min. Retention times: 0.54 min ((S)- and (R)-5-benzyl 1-tert-butyl 2-amino-pentanedioate), 2.17 min ((S)- and (R)-5-benzyl 1-tert-butyl 2-palmitamidopentanedioate).

b) (S)-5-tert-butoxy-5-oxo-4-palmitamidopentanoic acid

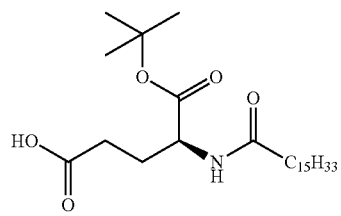

In 250-mL 3-necked flask, a mixture of crude (S)-5-benzyl 1-tert-butyl 2-palmitamidopentanedioate (13.2 g, 24.8 mmol), 10% palladium on charcoal (1.31 g, 1.20 mmol) and THF (150 mL) was stirred under hydrogen atmosphere at room temperature. As to TLC (EE/heptane 1:1, $R_F$ starting material=0.5, $R_F$ product=0.2, detected with aid of Komarowsky's reagent (cf. P. Stevens, *J. Chromatog.* 1964, 14, 269)), after 23 h the conversion was complete. The black suspension was passed through a fiberglass filter and the resulting colourless filtrate was evaporated to dryness to afford the crude product (11.3 g) which was then purified via crystallization from heptane to yield (S)-5-tert-butoxy-5-oxo-4-palmitamidopentanoic acid (8.78 g, 76% yield) as a white solid with 97.7% chemical purity (LC method see below).

M.p. 63° C.; EI-MS: m/z=440.33 (M−H)⁻.

LC method: X-Bridge phenyl column No. 823, 50×4.6 mm, ID 2.5 μm; mobile phase, A: water/NCMe (95:5), B: NCMe, C: water/glycine (pH 9); flow: 3 ml/min; gradient from 50/4/55 (A/B/C) to 7/88/5 (A/B/C) within 2 min, isocratic 7/88/5 (A/B/C) for 0.8 min. Retention times: 0.77 min ((S)- and (R)-5-tert-butoxy-5-oxo-4-palmitamidopentanoic acid), 2.17 min ((S)- and (R)-5-benzyl 1-tert-butyl 2-palmitamidopentanedioate).

c) (S)-allyl 2-(((9H-fluoren-9-yl)methoxy)carbonylamino)-6-((S)-5-tert-butoxy-5-oxo-4-palmitamidopentanamido)hexanoate

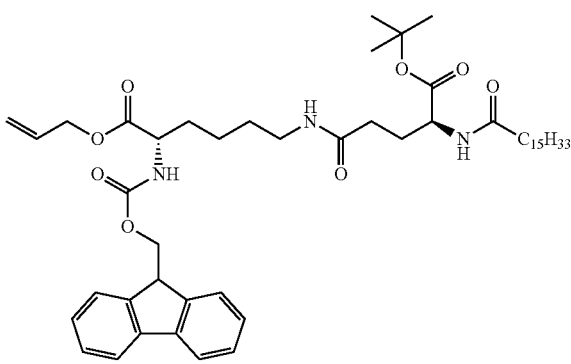

In a 500-mL 3-necked flask, a mixture of (S)-5-tert-butoxy-5-oxo-4-palmitamidopentanoic acid (8.77 g, 19.4 mmol), 1,1'-carbonyldiimidazole (3.30 g, 20.4 mmol) and DCM (125 mL) was stirred at room temperature for 90 min. To the resulting white suspension, a solution of (S)-allyl 6-amino-2-(((9H-fluoren-9-yl)methoxy)carbonylamino)-6-aminohexanoate (8.68 g, 19.5 mmol) and triethylamine (1.96 g, 19.4 mmol) in DCM (50 mL) was added within 15 min. The reaction mixture was stirred for another 90 min at r.t. to complete the conversion (determined via TLC (EE/heptane 1:1, $R_F$ starting material=0, $R_F$ product=0.5, detected with aid of Komarowsky's reagent (cf. P. Stevens, *J. Chromatog.* 1964, 14, 269)). Next, DCM (50 mL) and water (40 mL) was added to the mixture and the layers were separated. The aqueous layer was extracted with DCM (20 mL) and the combined organic layers dried over sodium sulphate. After evaporation off the solvent, the residual crude product (16.0 g) was purified by crystallization from diethyl ether to afford (S)-allyl 2-(((9H-fluoren-9-yl)methoxy)carbonylamino)-6-((S)-5-tert-butoxy-5-oxo-4-palmitamidopentanamido)hexanoate (15.2 g, 91%) as white solid with 96.5% chemical purity (LC method see below) and >99.9% enantio- and diastereomeric purity (chiral LC method see below).

M.p. 118° C.; EI-MS: m/z=832.55 (M+H)$^+$.

LC method: X-Bridge phenyl column, 50×4.6 mm, ID 2.5 μm; mobile phase, A: water/NCMe (95:5), B: NCMe, C: 0.1% formic acid in water; flow: 2 ml/min; gradient from 65/25/10 (A/B/C) to 10/80/10 (A/B/C) within 10 min, isocratic 10/80/10 (A/B/C) for 2 min. Retention times: 9.59 min ((S)-allyl 24(9H-fluoren-9-yl)methoxy)carbonylamino)-64 (S)-5-tert-butoxy-5-oxo-4-palmitamidopentanamido)hexanoate)).

Chiral LC method: Chiracel OD-RH columns No. 745 & No. 702, 150×4.6 mm, ID 5 μm; mobile phase, A: NCMe, B: water/HClO$_4$ (pH 2); flow: 1 ml/min, isocratic 68:32 (A/B) for 32 min, gradient from 68/32 (A/B) to 75/25 (A/B) within 0.5 min, isocratic 75/25 (A/B) for 29.5 min. Retention times: 45.39 min ((R)-allyl 2-(((9H-fluoren-9-yl)methoxy)carbonylamino)-6-((R)-5-tert-butoxy-5-oxo-4-palmitamidopentanamido)hexanoate), 47.75 min ((R)-allyl 2-(((9H-fluoren-9-yl)methoxy)carbonylamino)-6-((S)-5-tert-butoxy-5-oxo-4-palmitamidopentanamido)hexanoate), 51.98 min ((S)-allyl 2-(((9H-fluoren-9-yl)methoxy)carbonylamino)-6-((R)-5-tert-butoxy-5-oxo-4-palmitamidopentanamido)hexanoate), 55.66 min ((S)-allyl 2-(((9H-fluoren-9-yl)methoxy)carbonylamino)-6-((S)-5-tert-butoxy-5-oxo-4-palmitamidopentanamido)hexanoate).

Example 2

(S)-2-(((9H-fluoren-9-yl)methoxy)carbonylamino)-6-((S)-5-tert-butoxy-5-oxo-4-palmitamidopentanamido)hexanoic acid

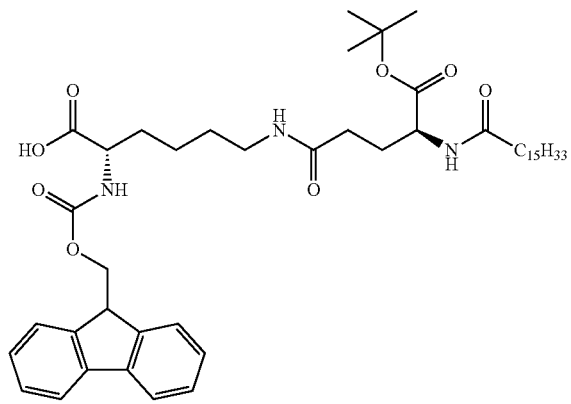

In a 500-mL 3-necked flask, a mixture of (S)-allyl 2-(((9H-fluoren-9-yl)methoxy)carbonylamino)-6-((S)-5-tert-butoxy-5-oxo-4-palmitamidopentanamido)hexanoate (10.0 g, 11.4 mmol), phenylsilane (7.02 g, 62.9 mmol), tetrakis(triphenylphosphine) palladium(0) (1.00 g, 0.85 mmol) and DCM (250 mL) was stirred at room temperature. As to TLC (EE/heptane 3:1, $R_F$ starting material=0.2, $R_F$ product=0, detected with UV at 254 nm), after 11 min the conversion was complete. The reaction mixture was diluted with DCM (50 mL) and washed successively with water (50 mL), aqueous sodium diethyldithiocarbamate (0.5%, 30 mL) and brine (30 mL), dried over sodium sulphate and rotatory evaporated to dryness. Digestion of the residual crude product first with heptane (25 mL) and afterwards with heptane/DCM (9:1) at at r.t. afforded after filtration and drying crude (S)-2-(((9H-fluoren-9-yl)methoxy)carbonylamino)-6-((S)-5-tert-butoxy-5-oxo-4-palmitamidopentanamido)hexanoic acid (8.92 g) with 77.2% chemical purity (LC method see below). The crude product contained 11% of triphenylphosphine oxide as major impurity. Preparative supercritical fluid chromatography (SFC, method see below) of a 1 g sample of the crude product afforded pure (S)-2-(((9H-fluoren-9-yl)methoxy)carbonylamino)-6-((S)-5-tert-butoxy-5-oxo-4-palmitamidopentanamido)hexanoic acid (0.75 g, 72%) as a white solid with 96.7% chemical purity (LC method see below), 98.0% enantiomeric and 99.8% diastereomeric purity (chiral LC method see below)

M.p. 119° C.; EI-MS: m/z=792.52 (M+H)$^+$.

LC method: X-Bridge phenyl column No. 823, 50×4.6 mm, ID 2.5 μm; mobile phase, A: water/NCMe (95:5), B: NCMe, C: 0.1% formic acid in water; flow: 2 ml/min; gradient from 65/25/10 (A/B/C) to 10/80/10 (A/B/C) within 10 min, isocratic 10/80/10 (A/B/C) for 2 min. Retention times: 8.65 min ((S)-2-(((9H-fluoren-9-yl)methoxy)carbonylamino)-6-((S)-5-tert-butoxy-5-oxo-4-palmitamidopentanamido)hexanoic acid), 9.59 min ((S)-allyl 2-(((9H-fluoren-9-yl)methoxy)carbonylamino)-6-((S)-5-tert-butoxy-5-oxo-4-palmitamidopentanamido)hexanoate)).

Chiral LC method: Chiracel OD-RH columns No. 745 & No. 702, 150×4.6 mm, ID 5 μm; mobile phase, A: NCMe, B: water/HClO$_4$ (pH 2); flow: 1 ml/min, isocratic 68:32 (A/B) for 32 min, gradient from 68/32 (A/B) to 75/25 (A/B) within 0.5 min, isocratic 75/25 (A/B) for 29.5 min. Retention times: 21.56 min ((R)-24(9H-fluoren-9-yl)methoxy)carbonylamino)-6-((R)-5-tert-butoxy-5-oxo-4-palmitamidopentanamido)hexanoic acid), 23.52 min ((R)-2-(((9H-fluoren-9-yl)methoxy)carbonylamino)-6-((S)-5-tert-butoxy-5-oxo-4-palmitamidopentanamido)hexanoic acid), 25.68 min ((S)-2-(((9H-fluoren-9-yl)methoxy)carbonylamino)-6-((R)-5-tert-butoxy-5-oxo-4-palmitamidopentanamido)hexanoic acid), 28.32 min ((S)-2-(((9H-fluoren-9-yl)methoxy)carbonylamino)-6-((S)-5-tert-butoxy-5-oxo-4-palmitamidopentanamido)hexanoic acid)

Preparative SFC method: Viridis 2-ethylpyridine OBD column, 150×30 mm, ID 5 μm; 50° C. column temperature; mobile phase, A: CO$_2$, B: MeOH; flow: 60 ml/min, gradient from 80:20 (A/B) to 60/40 (A/B) within 10 min.

Example 3

(S)-2-(((9H-fluoren-9-yl)methoxy)carbonylamino)-6-((S)-5-tert-butoxy-5-oxo-4-palmitamidopentanamido)hexanoic acid

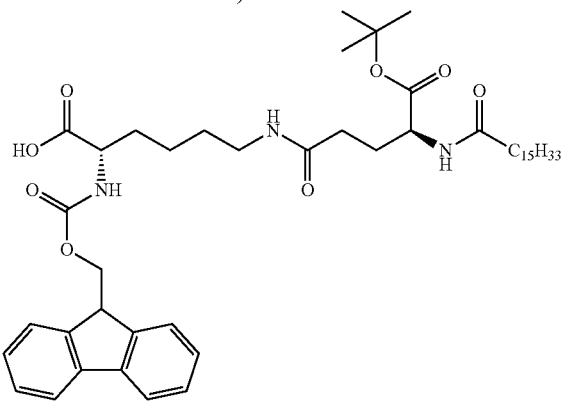

In a 250-mL 3-necked flask, a mixture of (S)-allyl 2-(((9H-fluoren-9-yl)methoxy)carbonylamino)-6-((S)-5-tert-butoxy-5-oxo-4-palmitamidopentanamido)hexanoate (12.0 g, 13.7 mmol), phenylsilane (2.28 g, 20.4 mmol), tetrakis(triphenylphosphine) palladium(0) (96.0 mg, 0.08 mmol) and DCM (120 mL) was stirred at r.t. As to TLC (DCM/MeOH 9:1, $R_F$ starting material=0.9, $R_F$ product=0.3, detected with UV at 254 nm), after 3 h the conversion was complete. The reaction mixture was then washed successively with aqueous sodium diethyldithiocarbamate (0.5%, 20 mL) and brine (75 mL), dried over sodium sulphate and rotatory evaporated to dryness to yield crude (S)-2-(((9H-fluoren-9-yl)methoxy)carbonylamino)-6-((S)-5-tert-butoxy-5-oxo-4-palmitamidopentanamido)hexanoic acid (11.6 g) with 93.5% chemical purity (LC method see Example 2), >99.9% enantiomeric and 99.7% diastereomeric purity (chiral LC method see Example 2) containing 1.2% of residual triphenylphosphine oxide. The crude product was then suspended in heptane (230 mL) for 1 h at r.t, the mixture was filtered and the filter cake was washed with heptane (50 mL) to yield (S)-2-(((9H-fluoren-9-yl)methoxy)carbonylamino)-6-((S)-5-tert-butoxy-5-oxo-4-palmitamidopentanamido)hexanoic acid (10.9 g, 97% yield) as a yellowish solid with 96.2% chemical purity (LC method see Example 2), >99.9% enantiomeric and 99.8% diastereomeric purity (chiral LC method see Example 2) containing 0.8% of residual triphenylphosphine oxide.

M.p. 119° C.; EI-MS: m/z=792.52 (M+H)$^+$.

Example 4

((R)-allyl 2-(((9H-fluoren-9-yl)methoxy)carbonylamino)-6-((S)-5-tert-butoxy-5-oxo-4-palmitamidopentanamido)hexanoate

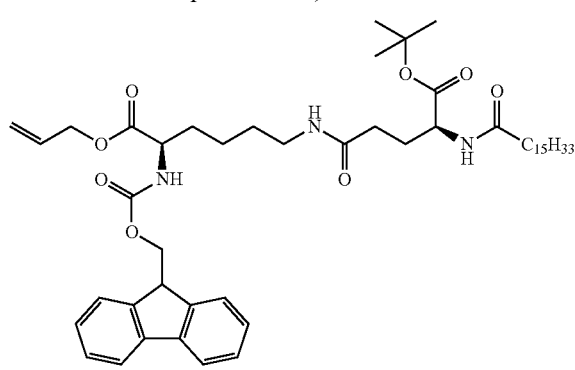

In a 25-mL 3-necked flask, a mixture of (S)-5-tert-butoxy-5-oxo-4-palmitamidopentanoic acid (500 mg, 1.12 mmol), 1-hydroxybenzotriazole (175 mg, 1.14 mmol), 1,1'-carbonyldiimidazole (200 mg, 1.23 mmol) and DCM (10 mL) was stirred at room temperature for 90 min. To the resulting white suspension, a solution of (R)-allyl 6-amino-2-(((9H-fluoren-9-yl)methoxy)carbonylamino)-6-aminohexanoate (507 mg, 1.12 mmol) and triethylamine (113 mg, 1.12 mmol) in DCM (5 mL) was added within 5 min. The reaction mixture was stirred for another 60 min at room temperature to complete the conversion (determined via TLC (DCM/MeOH 95:5, $R_F$ starting material=0, $R_F$ product=0.2, detected with UV at 254 nm). Next, water (10 mL) was added to the mixture and the layers were separated. The aqueous layer was extracted with DCM (30 mL) and the combined organic layers dried over sodium sulphate. After evaporation off the solvent, the residual crude product (983 mg) was purified by crystallization from diethyl ether to afford (R)-allyl 2-(((9H-fluoren-9-yl)methoxy)carbonylamino)-6-((S)-5-tert-butoxy-5-oxo-4-palmitamidopentanamido)hexanoate (686 mg, 70%) as white solid with 94.2% chemical purity (LC method see below) and >99.9% enantio- and diastereomeric purity (chiral LC method see Example 1c)

M.p. 114° C.; EI-MS: m/z=832.54 (M+H)$^+$.

LC method: X-Bridge phenyl column, 50×4.6 mm, ID 2.5 μm; mobile phase, A: water/NCMe (95:5), B: NCMe, C: 0.1% formic acid in water; flow: 2 ml/min; gradient from 65/25/10 (A/B/C) to 10/80/10 (A/B/C) within 10 min, isocratic 10/80/10 (A/B/C) for 2 min. Retention times: 9.55 min ((R)-allyl 2-(((9H-fluoren-9-yl)methoxy)carbonylamino)-6-((S)-5-tert-butoxy-5-oxo-4-palmitamidopentanamido)hexanoate)).

Example 5

(R)-2-(((9H-fluoren-9-yl)methoxy)carbonylamino)-6-((S)-5-tert-butoxy-5-oxo-4-palmitamidopentanamido)hexanoic acid

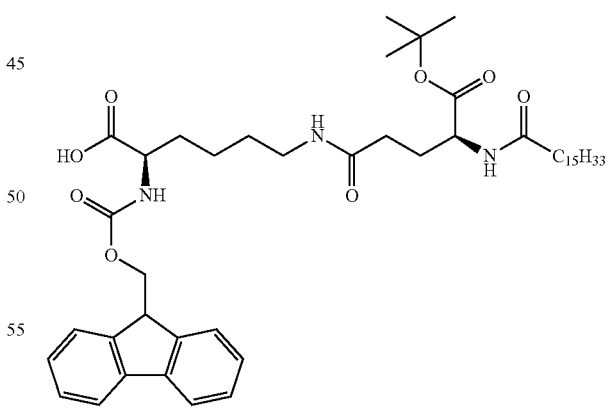

In a 25-mL 3-necked flask, a mixture of (R)-allyl 2-(((9H-fluoren-9-yl)methoxy)carbonylamino)-6-((S)-5-tert-butoxy-5-oxo-4-palmitamidopentanamido)hexanoate (675 mg, 0.76 mmol), phenylsilane (351 mg, 3.14 mmol), tetrakis(triphenylphosphine) palladium(0) (20.0 mg, 0.02 mmol) and DCM (7 mL) was stirred at 10° C. As to TLC (DCM/MeOH 95:5, $R_F$ starting material=0.8, $R_F$ product=0.2, detected with UV at 254 nm), after 25 min the conversion was complete. After additional 15 min, the reaction mixture was diluted with DCM (10 mL) and washed successively with water (10 mL), a aqueous of sodium diethyldithiocarbamate (0.5%, 10 mL) and brine (10 mL). The organic solution was dried over sodium sulphate and rotatory evaporated to dryness to yield crude (R)-2-(((9H-fluoren-9-yl)methoxy)carbonylamino)-6-((S)-5-tert-butoxy-5-oxo-4-palmitamidopentanamido)hexanoic acid (631 mg) with 87.4 chemical purity (LC method see below)), >99.9% enantiomeric and 98.8% diastereomeric purity (chiral LC method see Example 2). The crude product contained 6% of triphenylphosphine oxide as major impurity. Preparative supercritical fluid chromatography (SFC, method see Example 2) of a 603 mg sample of the crude product afforded pure (R)-2-(((9H-fluoren-9-yl)methoxy)carbonylamino)-6-((S)-5-tert-butoxy-5-oxo-4-palmitamidopentanamido)hexanoic acid (348 mg, 59%) as a white solid with 98.7% chemical purity (LC method see below), >99.9% enantiomeric and 99.4% diastereomeric purity (chiral LC method see Example 2)

M.p. 125° C.; EI-MS: m/z=792.52 (M+H)$^+$.

LC method: X-Bridge phenyl column, 50×4.6 mm, ID 2.5 μm; mobile phase, A: water/NCMe (95:5), B: NCMe, C: 0.1% formic acid in water; flow: 2 ml/min; gradient from 65/25/10 (A/B/C) to 10/80/10 (A/B/C) within 10 min, isocratic 10/80/10 (A/B/C) for 2 min. Retention times: 8.33 min ((R)-2-(((9H-fluoren-9-yl)methoxy)carbonylamino)-6-((S)-5-tert-butoxy-5-oxo-4-palmitamidopentanamido)hexanoic acid), 9.35 min ((R)-allyl 2-(((9H-fluoren-9-yl)methoxy)carbonylamino)-6-((S)-5-tert-butoxy-5-oxo-4-palmitamidopentanamido)hexanoate)).

The invention claimed is:

1. A process for the preparation of compounds of formula I,

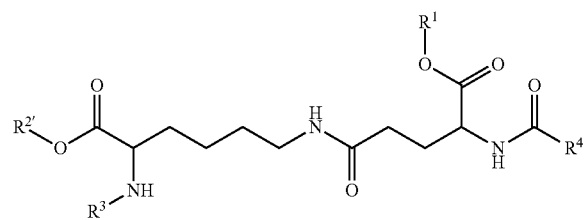

and enantiomers and salts thereof, wherein:
$R^1$ is hydrogen or an ester protecting group;
$R^2$ is hydrogen;
$R^3$ is hydrogen or an amino protecting group and
$R^4$ is $C_{12-20}$-alkyl;
the process comprising:
a) coupling the glutamic acid derivative of formula II

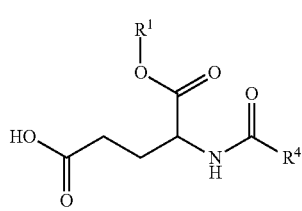

or a salt thereof with a lysine derivative of formula III

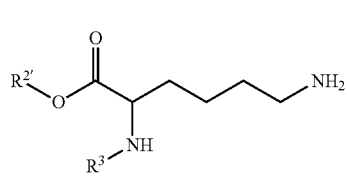

wherein $R^{2'}$ is an ester protecting group, or a salt thereof to form a compound of the formula Ic;

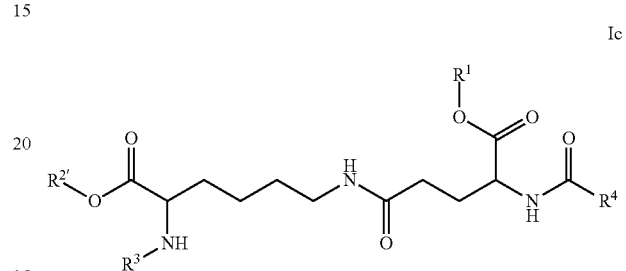

and b) removing the ester protecting group $R^{2'}$ to provide the compound of formula I.

2. The process of claim 1, wherein the ester protecting group is selected from $C_{1-4}$-alkyl, optionally substituted with phenyl, $C_{2-4}$-alkenyl, piperidinyl or dimethylaminoboranyl.

3. The process of claim 1, wherein $R^1$ is hydrogen or $C_{1-4}$-alkyl.

4. The process of claim 1, wherein $R^1$ is $C_{1-4}$-alkyl.

5. The process of claim 1, wherein $R^1$ is hydrogen.

6. The process of claim 1, wherein $R^3$ is 9H-fluoren-9-ylmethoxycarbonyl.

7. The process of claim 1, wherein $R^1$ is t-butyl.

8. The process of claim 1, wherein $R^4$ is $C_{14-16}$-alkyl.

9. The process of claim 1, wherein $R^4$ is $C_{15}$-alkyl.

10. The process of claim 1, wherein $R^4$ is pentadecyl.

11. The process of claim 1, wherein $R^3$ is 9H-fluoren-9-ylmethoxycarbonyl and $R^4$ is $C_{15}$-alkyl.

12. The process of claim 1, wherein $R^3$ is 9H-fluoren-9-ylmethoxycarbonyl and $R^4$ is pentadecyl.

13. The process of claim 1, wherein the compound of formula I is a compound of formula Ia

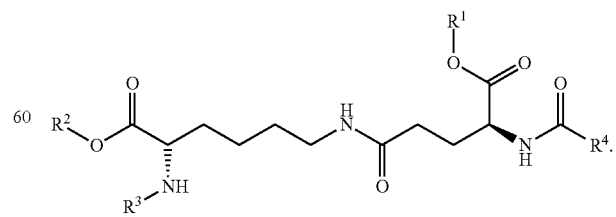

14. The process of claim 1, wherein the compound of formula I is a compound of formula Ib

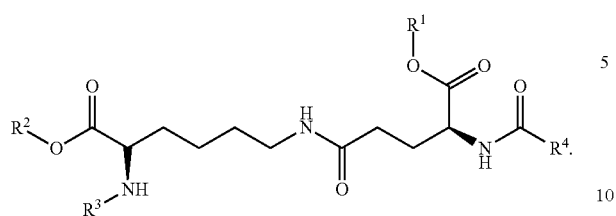
Ib
15. The process of claim 1, wherein the coupling of the glutamic acid derivative of formula II with the lysine derivative of formula III is carried out by solid phase synthesis.
16. The process of claim 1, wherein the coupling of the glutamic acid derivative of formula II with the lysine derivative of formula III is carried out by FMOC solid phase synthesis.
* * * * *